United States Patent [19]

Ermert et al.

[11] Patent Number: 4,913,154
[45] Date of Patent: Apr. 3, 1990

[54] MEDICAL EXAMINATION INSTALLATION WITH IMPROVED IMAGE CONTRAST

[75] Inventors: Helmut Ermert, Roettenbach; Manfred Pfeiler; Karl Barth, both of Erlangen, all of Fed. Rep. of Germany

[73] Assignee: Siemens Aktiengesellschaft, Berlin and Munich, Fed. Rep. of Germany

[21] Appl. No.: 249,516

[22] Filed: Sep. 26, 1988

[30] Foreign Application Priority Data

Nov. 19, 1987 [DE] Fed. Rep. of Germany ....... 3739229

[51] Int. Cl.$^4$ .............................................. A61B 6/00
[52] U.S. Cl. .................................... 128/654; 358/111; 378/99
[58] Field of Search ........................ 128/653, 654, 659; 378/99; 358/111

[56] References Cited

U.S. PATENT DOCUMENTS

| | | | |
|---|---|---|---|
| 3,847,138 | 11/1974 | Gollub | 128/654 |
| 3,859,985 | 1/1975 | Eckhart . | |
| 4,044,757 | 8/1977 | McWhorter et al. . | |
| 4,483,342 | 11/1984 | Pfeifer . | |
| 4,514,759 | 4/1985 | Amtmann . | |
| 4,611,340 | 9/1986 | Okazaki . | |
| 4,671,256 | 6/1987 | Lemelson | 128/654 |

FOREIGN PATENT DOCUMENTS 0121216 10/1984 European Pat. Off. .

*Primary Examiner*—Ruth S. Smith
*Attorney, Agent, or Firm*—Hill, Van Santen, Steadman & Simpson

[57] ABSTRACT

A medical installation for examining a patient irradiates at least a portion of the patient with an examination field, and detects the attenuated field and generates an image therefrom. During exposure of the patient to the examination field, a contrast agent injector is operated to intermittently inject contrast agent into the patient at a selected frequency. The image is generated of the patient at an image pick-up frequency, and the frequency of injection of the contrast agent may be matched to, or differ from, the image pick-up frequency. The liquid injected into the patient will have alternating sections with and without contrast agent following in succession.

8 Claims, 1 Drawing Sheet

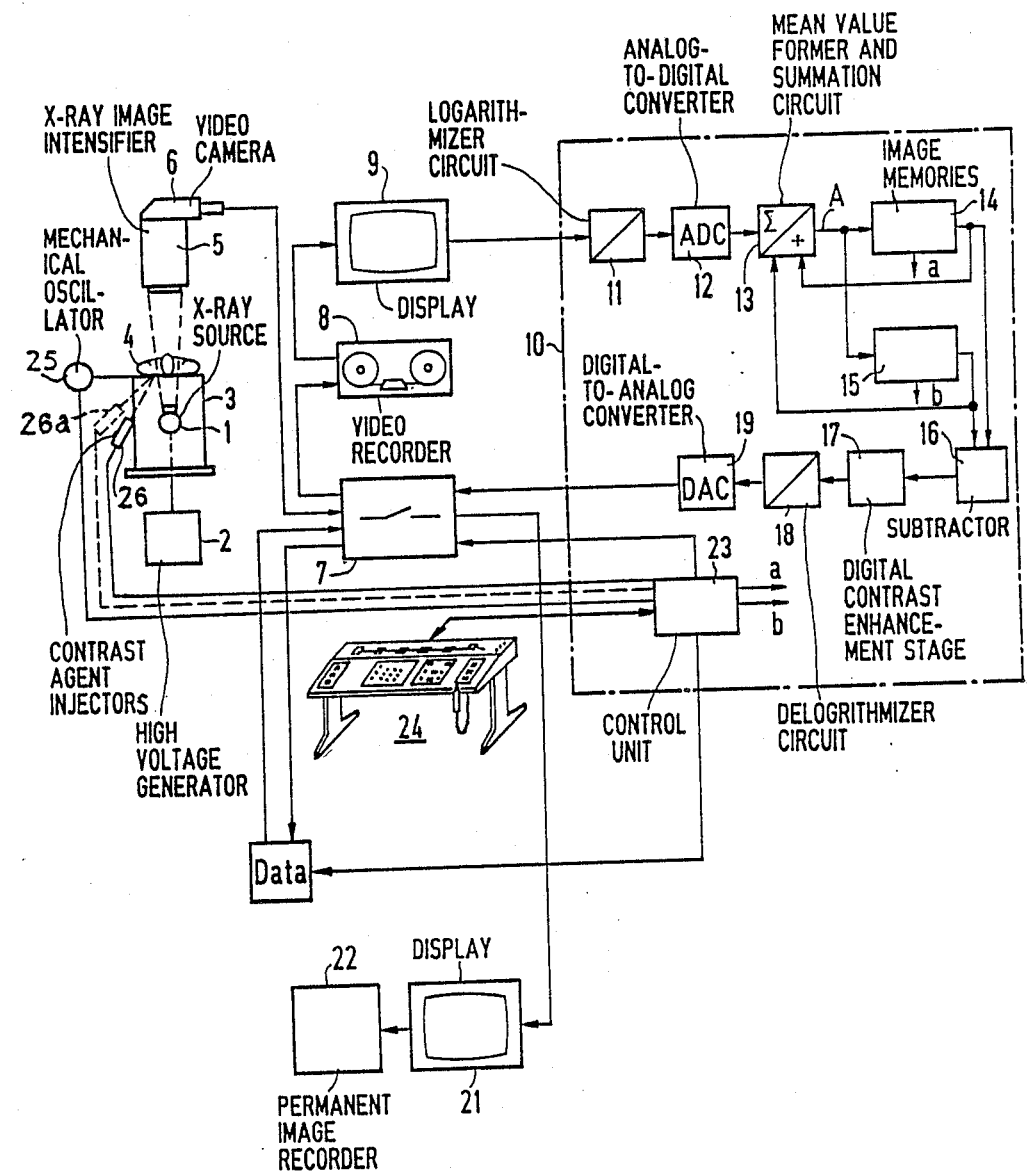

2

MEDICAL EXAMINATION INSTALLATION WITH IMPROVED IMAGE CONTRAST

BACKGROUND OF THE INVENTION

1. Field of the Invention

The present invention is directed to a medical examination installation for generating visual images of at least a portion of an examination subject, which uses an image pick-up system to obtain and process such images.

2. Related Application

The present application is related to an application having Ser. No. 249,515 entitled Medical Examination Installation With Improved Image Contrast, Ermert et al, filed simultaneously herewith.

3. Description of the Prior Art

Images of a body portion can be continuously produced with a medical examination installation, for example an x-ray installation. Body parts which exhibit only a slight contrast relative to neighboring tissue are inadequately represented in such images. For example, gallstones are frequently difficult to localize. It is required for modern therapy methods, for example lithotripsy, to be able to clearly visually display such body parts so that an exact positioning of the treatment instrument, such as a shock wave generator, can be achieved. Such exact placement is necessary, for example, for calculus disintegration.

SUMMARY OF THE INVENTION

It is an object of the present invention to provide an medical examination system wherein body parts having a low contrast relative to the surrounding tissue can be represented with an improved contrast.

The above object is achieved in accordance with the principles of the present invention in an examination installation wherein the patient to be examined is intermittently injected with contrast agent during an exposure time of the patient which is undertaken to generate an image in an imaging system. The frequency of the contrast agent injection may be the same as the image pick-up frequency of the image system. The intermittent contrast agent injection can be accomplished using a single syringe which is intermittently (i.e., non-continuously) operated so that each brief period of contrast agent injection is followed by a brief period wherein n o contrast agent is injected, or the intermittent injection can be undertaken using two syringes operated in alternation, with one of the syringes containing the contrast agent and the other syringe containing a liquid other than contrast agent.

DESCRIPTION OF THE DRAWING

The single Figure is a schematic block diagram of a medical examination installation constructed in accordance with the principles of the present invention.

DESCRIPTION OF THE PREFERRED EMBODIMENTS

As shown in the drawing, a medical examination installation includes an x-ray tube 1 which is supplied by a high voltage generator 2, and generates x-rays which irradiate a patient 4 disposed on a patient support table 3. An image intensifier/video chain includes an x-ray image intensifier 5 with a video camera 6 attached thereto for recording the x-ray images and converting them into a video signal which is supplied to a switching stage 7. The switching stage 7 functions as a video signal distributor, and, depending upon the setting thereof, permits the signals corresponding to the x-ray images to be recorded on a video recorder 8 and supplied to a television monitor 9.

For generating differential images, the video signals in real time, or from the video recorder 8, are supplied to an image subtraction stage 10. The image subtraction stage 10 has a logarithmizer 11 which forms the input of the stage. The output signal of the logarithmizer 11 is supplied to an analog-to-digital converter 12. The logarithmizer 11 generates signals which are proportional to the sum of the products of a mass attenuation coefficient and the ass of all substances disposed in the beam path. The output of the converter 12 is supplied to a mean value former and summation circuit 13 which assigns a sliding, weighted mean value to the signals for improving the signal-to-noise ratio. The signals acquired in this manner are stored in two image memories 14 and 15, which are connected to a subtractor 16. The output of the subtractor 16 is supplied to the switching stage 7 via a digital contrast enhancement stage 17, such as a window amplifier, a delogarithmizer 18, and a digital-to-analog converter 19. The switching stage 7 directs the signals to a further television monitor 21 for display. The subtraction images can be permanently retained using a permanent image recorder 22, such as a photography device or other type of image pick-up unit.

A control unit 23 controls the entry of successive images into the memories 14 and 15 in such a manner that chronologically successive images are alternately entered into the memories 14 and 15, and overwrite the respective memory contents. Continuous reproduction of a differential image in real time accordingly ensues on the monitor 21.

The installation explained thus far corresponds to that described in U.S. Pat. No. 4,483,342.

In accordance with the principles of the present invention, the patient support table 3 is mounted so as to be vibratable, and is connected to a mechanical oscillator 25, i.e., vibration generator, which is controlled by the control unit 23. The patient 4 on the table 3, or a selected region thereof corresponding to the region being irradiated by the x-ray source 1, is placed in vibration. The frequency of the mechanical vibrations may be the same as the image pick-up frequency of the video camera 6, or may differ therefrom such as being half of that image frequency. Body parts which are different in terms of their mechanical properties vibrate with different amplitudes and phases. A continuous subtraction of the images accordingly leads to an image sequence on the monitor 21 wherein the different body parts are portrayed with differently fashioned borders as a result of their different vibrational properties. Calculi in an organ will usually deviate particularly clearly from the surrounding tissue in terms of their vibrational behavior, and will therefore have especially clear borders on the displayed image.

The frequency relation discussed above is only by way of example. The frequencies will be selected based on the mechanical properties of the body part to be imaged in order to achieve the best imaging properties.

The amplitude and frequency of the mechanical vibration of the support table 3, and thus of the patient 4, can be set at a control console 24, by which the entire installation is controlled and monitored.

The above-described image subtraction technique is only one possibility of portraying body parts having different mechanical vibrational behavior. It is also possible to achieve similar results using selective filtering.

In order to portray vessels of the patient 4, a contrast agent injector 26 is mounted at the patient support table 3. The contrast agent injector 26 is also controlled by the control unit 23. The control unit 23 is operated such that the contrast agent injector 26 intermittently injects contrast agent into the corresponding vessel during an exposure of the patient 4 using the above-described image generating system. The injection frequency is matched to the image pick-up frequency, or may differ therefrom, and is also set at the control console 24. The blood vessels into which the contrast agent is intermittently injected will thus appear in the displayed image as alternating bright and dark paths, which can be easily identified.

Due to the advance of the contrast agent column in the vessel, the column being interrupted at uniform intervals, the density in the body part under examination fluctuates at a frequency determined, for a given interruption frequency, by the blood vessel flow rate. As a result of the subsequent processing with the above-described image subtraction technique, the blood vessels will be made clearer on the displayed images. This occurs continuously without masks having to be entered into the image memories 14 and 15.

The contrast agent injector may be a double syringe injector wherein two syringe 26 and 26a are connected to a common distributor, which leads to the patient. One of the syringes contains contrast agent, and the other syringe contains another liquid, and the syringes are operated in alternation so that the stream of liquid injected into the patient has portions with and without contrast agent following in alternating succession. The contrast agent injector 26 may also be a single syringe which is operated intermittently to inject contrast agent into said patient at intervals, so that the blood vessel has sections with and without contrast agent, again following each other in alternating succession.

It is also within the framework of the present invention to use image pick-up systems other than the type shown in the exemplary embodiment. An ultrasound image pick-up system, for example, may be used for image production instead of the image intensifier/video chain.

Although modifications and changes may be suggested by those skilled in the art it is the intention of the inventors to embody within the patent warranted hereon all changes and modifications as reasonably and properly come within the scope of their contribution to the art.

We claim as out invention:

1. A medical installation for examining a patient comprising:
    means adapted for subjecting at least a portion of said patient to an examination field during an exposure time;
    means for detecting said examination field attenuated by said patient;
    means connected to said means for detecting for generating a visual image of said portion of said patient; and
    means for intermittently injecting contrast agent into said patient at least during said exposure time at a selected frequency.

2. An installation as claimed in claim 1, wherein said means for generating an image operates at an image pick-up frequency, and wherein said means for intermittently injecting contrast agent into said patient is a means for intermittently injecting contrast agent into said patient at a frequency equal to said image pick-up frequency.

3. An installation as claimed in claim 1, wherein said means for generating an image operates at an image pick-up frequency, and wherein said means for intermittently injecting contrast agent into said patient is a means for intermittently injecting contrast agent into said patient at a frequency different from said image pick-up frequency.

4. An installation as claimed in claim 1, wherein said means for injecting contrast agent, comprises two syringes connected to a common distributor adapted for connection to said patient, one of said syringes containing contrast agent and the other of said syringes containing a liquid other than contrast agent, and means for operating said syringes in alternation.

5. An installation as claimed in claim 1, wherein said means for intermittently injecting contrast agent is a single syringe operated to inject contrast agent at intervals.

6. An installation as claimed in claim 1, wherein said means for generating an image includes means for producing differential images from chronologically successive images from said means for detecting.

7. An installation as claimed in claim 1, wherein said means for generating an examination field is a source of x-rays.

8. A method for examining a patient comprising the steps of:
    placing at least a portion of said patient in an examination field for an exposure time;
    detecting said examination field attenuated by said patient;
    intermittently injecting contrast agent into said patient at a selected frequency during said exposure time; and
    generating an image of said portion of said patient from signals from said means for detecting.

* * * * *